United States Patent
Oba et al.

(10) Patent No.: US 8,858,621 B2
(45) Date of Patent: Oct. 14, 2014

(54) METHODS OF IMPLANTING A PROSTHETIC HEART VALVE

(71) Applicant: Edwards Lifesciences Corporation, Irvine, CA (US)

(72) Inventors: Travis Zenyo Oba, Corona, CA (US); Louis A. Campbell, Santa Ana, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 0 days.

(21) Appl. No.: 13/918,509

(22) Filed: Jun. 14, 2013

(65) Prior Publication Data

US 2013/0282112 A1 Oct. 24, 2013

Related U.S. Application Data

(62) Division of application No. 12/839,194, filed on Jul. 19, 2010, now abandoned.

(60) Provisional application No. 61/228,072, filed on Jul. 23, 2009.

(51) Int. Cl.
*A61F 2/24* (2006.01)
*A61B 17/34* (2006.01)

(52) U.S. Cl.
CPC .......... *A61F 2/2427* (2013.01); *A61B 17/3468* (2013.01); *A61B 2017/3425* (2013.01); *A61B 17/3423* (2013.01); *A61F 2/2433* (2013.01); *A61B 17/3439* (2013.01)
USPC .......................................... 623/2.11; 606/148

(58) Field of Classification Search
USPC ............. 623/1.11, 1.12, 1.23, 2.11, 2.17, 2.2, 623/2.38, 2.4, 2.41, 11.11; 604/160, 604/164.01, 164.03, 264, 510, 523; 606/108, 148
See application file for complete search history.

(56) References Cited

U.S. PATENT DOCUMENTS 3,049,013 A 8/1962 Berry
3,164,009 A 1/1965 Schaschl
(Continued)

FOREIGN PATENT DOCUMENTS

EP 2080474 A1 7/2009
GB 2083362 A 3/1982
(Continued)

OTHER PUBLICATIONS

Berdat, Pascal A., et. al. "Off-pump pulmonary valve replacement with the new Shelhigh Injectable Stented Pulmonic Valve," The Journal of Thoracic and Cardiovascular Surgery, May 2006, pp. 1192-1193, vol. 131, No. 5, Bern Switzerland.

*Primary Examiner* — Dianne Dornbusch
*Assistant Examiner* — Robert Lynch
(74) *Attorney, Agent, or Firm* — AnneMarie Kaiser; Guy Cumberbatch

(57) ABSTRACT

The present disclosure concerns embodiments and methods of use of an introducer that is adapted to facilitate insertion of a prosthetic device, such as a prosthetic heart valve, into a patient's vasculature. In one embodiment, the introducer comprises an elongated body defining a central lumen extending between distal and proximal ends of the body. The introducer body can also have a longitudinally extending gap extending along the length of the body between the distal end proximal ends. The gap in the introducer allows a user to place the introducer around implant sutures by passing the sutures through the gap and into the central lumen. Similarly, the gap allows the introducer to be easily removed from the sutures and/or a delivery device by passing them outwardly through the gap.

14 Claims, 15 Drawing Sheets

(56) References Cited

U.S. PATENT DOCUMENTS

| | | | |
|---|---|---|---|
| 3,409,013 A | 11/1968 | Berry | |
| 3,587,115 A | 6/1971 | Shiley | |
| 3,671,979 A | 6/1972 | Moulopoulos | |
| 4,016,867 A | 4/1977 | King et al. | |
| 4,056,854 A | 11/1977 | Boretos et al. | |
| 4,185,638 A | 1/1980 | Bruner | |
| 4,211,241 A | 7/1980 | Kaster et al. | |
| 4,243,050 A | 1/1981 | Littleford | |
| 4,306,562 A | 12/1981 | Osborne | |
| 4,362,167 A | 12/1982 | Nicolai et al. | |
| 4,566,465 A | 1/1986 | Arhan et al. | |
| 4,581,025 A | 4/1986 | Timmermans | |
| 4,631,052 A | 12/1986 | Kensey | |
| 4,643,194 A | 2/1987 | Fogarty | |
| 4,798,554 A | 1/1989 | Nelson et al. | |
| 4,813,401 A | 3/1989 | Grieshaber | |
| 4,883,458 A | 11/1989 | Shiber | |
| 4,921,479 A | 5/1990 | Grayzel | |
| 4,940,459 A | 7/1990 | Noce | |
| 5,010,892 A | 4/1991 | Colvin et al. | |
| 5,032,128 A | 7/1991 | Alonso | |
| 5,042,161 A | 8/1991 | Hodge | |
| 5,089,015 A | 2/1992 | Ross | |
| 5,360,014 A | 11/1994 | Sauter et al. | |
| 5,370,685 A | 12/1994 | Stevens | |
| 5,489,296 A | 2/1996 | Love et al. | |
| 5,531,785 A | 7/1996 | Love et al. | |
| 5,545,214 A | 8/1996 | Stevens | |
| 5,716,417 A | 2/1998 | Girard et al. | |
| 5,797,920 A | 8/1998 | Kim | |
| 5,814,098 A | 9/1998 | Hinnenkamp et al. | |
| 5,885,228 A | 3/1999 | Rosenman et al. | |
| 6,010,511 A | 1/2000 | Murphy | |
| 6,010,531 A | 1/2000 | Donlon et al. | |
| 6,019,739 A | 2/2000 | Rhee et al. | |
| 6,042,554 A | 3/2000 | Rosenman et al. | |
| 6,045,576 A | 4/2000 | Starr et al. | |
| 6,050,973 A | 4/2000 | Duffy | |
| 6,110,200 A | 8/2000 | Hinnenkamp | |
| 6,136,017 A | 10/2000 | Craver et al. | |
| 6,210,338 B1 | 4/2001 | Afremov et al. | |
| 6,224,586 B1 | 5/2001 | Stephens | |
| 6,319,281 B1 | 11/2001 | Patel | |
| 6,322,526 B1 | 11/2001 | Rosenman et al. | |
| 6,350,281 B1 | 2/2002 | Rhee | |
| 6,449,865 B1 | 9/2002 | Heckman | |
| 6,582,419 B1 | 6/2003 | Schoon et al. | |
| 6,589,212 B1 * | 7/2003 | Navis | 604/164.01 |
| 6,598,307 B2 | 7/2003 | Love et al. | |
| 6,942,694 B2 | 9/2005 | Liddicoat et al. | |
| 7,007,396 B2 | 3/2006 | Rudko et al. | |
| 7,025,780 B2 | 4/2006 | Gabbay | |
| 7,144,386 B2 | 12/2006 | Korkor et al. | |
| 7,258,698 B2 | 8/2007 | Lemmon | |
| 7,270,142 B2 | 9/2007 | Acosta | |
| 7,510,572 B2 | 3/2009 | Gabbay | |
| 7,662,160 B2 | 2/2010 | Bojarski et al. | |
| 7,713,216 B2 | 5/2010 | Dubey et al. | |
| 8,057,396 B2 | 11/2011 | Forster et al. | |
| 8,449,625 B2 | 5/2013 | Campbell et al. | |
| 8,475,521 B2 | 7/2013 | Suri et al. | |
| 2002/0020074 A1 | 2/2002 | Love et al. | |
| 2004/0073286 A1 | 4/2004 | Armstrong et al. | |
| 2005/0154441 A1 | 7/2005 | Schaeffer et al. | |
| 2006/0106415 A1 | 5/2006 | Gabbay | |
| 2006/0195134 A1 | 8/2006 | Crittenden | |
| 2007/0219629 A1 | 9/2007 | Bokros et al. | |
| 2007/0225659 A1 | 9/2007 | Melsheimer | |
| 2007/0225801 A1 * | 9/2007 | Drews et al. | 623/2.11 |
| 2007/0239254 A1 | 10/2007 | Chia et al. | |
| 2007/0299513 A1 | 12/2007 | Ryan et al. | |
| 2008/0021552 A1 * | 1/2008 | Gabbay | 623/11.11 |
| 2008/0082164 A1 * | 4/2008 | Friedman | 623/2.11 |
| 2008/0255580 A1 | 10/2008 | Hoffman et al. | |
| 2009/0093877 A1 | 4/2009 | Keidar et al. | |
| 2009/0132036 A1 | 5/2009 | Navia | |
| 2009/0182419 A1 | 7/2009 | Bolling | |
| 2009/0192600 A1 | 7/2009 | Ryan | |
| 2009/0192602 A1 | 7/2009 | Kuehn | |
| 2009/0192603 A1 | 7/2009 | Ryan | |
| 2009/0192604 A1 | 7/2009 | Gloss | |
| 2010/0152844 A1 | 6/2010 | Couetil | |
| 2011/0238166 A1 | 9/2011 | Gabbay | |
| 2011/0282438 A1 | 11/2011 | Drews et al. | |

FOREIGN PATENT DOCUMENTS

| | | |
|---|---|---|
| WO | 9640006 A1 | 12/1996 |
| WO | 9725003 A1 | 7/1997 |
| WO | 9741801 A1 | 11/1997 |
| WO | 9742871 A1 | 11/1997 |
| WO | 2010090720 A1 | 8/2010 |
| WO | 2010111621 A1 | 9/2010 |
| WO | 2011106354 A1 | 9/2011 |

* cited by examiner

METHODS OF IMPLANTING A PROSTHETIC HEART VALVE

RELATED APPLICATION DATA

The present application is a divisional of U.S. patent application Ser. No. 12/839,194, filed Jul. 19, 2010, which claims priority under 35 U.S.C. §119(e) to U.S. provisional application No. 61/228,072 filed Jul. 23, 2009.

FIELD

The present invention pertains to an introducer that can be used to facilitate implantation of a prosthetic heart valve.

BACKGROUND

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death.

When a native valve is replaced, surgical implantation of a prosthetic valve typically requires an open-chest surgery during which the heart is stopped and patient placed on cardiopulmonary bypass (a so-called "heart-lung machine"). In one common surgical procedure, an incision is made in the aorta and the diseased native valve leaflets are excised. An array of implant sutures are secured around the periphery of the native valve, and the opposite ends of the sutures are pulled through the incision and then threaded through the sewing ring of the prosthetic valve. The prosthetic valve is then "parachuted" down the array of sutures until it rests against the native annulus. Thereafter, the sutures can be tied off and severed to secure the prosthetic valve to the annulus.

One specific technique that is used to introduce the prosthetic valve into the aorta is referred to as the "shoehorn" technique. In the shoehorn technique, a transverse incision is made in the aortic root, which typically is smaller than the cross-sectional profile of the prosthetic valve. In order to pass the valve through the incision, the valve is inserted into the aortic root at an angle relative to a plane defined by the incision, much like passing a button through a button hole. As can be appreciated, this technique adds complexity to the procedure, can cause laceration of the tissue, and can cause damage to the prosthetic valve.

Another technique used to implant a prosthetic valve involves making an oblique or "hockey stick" shaped incision in the aorta. This type of incision creates a larger opening for the passage of the valve, but is more difficult to close and therefore is more prone to leakage than a straight transverse incision.

Accordingly, there exists a need for new and improved apparatus and methods for introducing a prosthetic valve into the vasculature of a patient.

SUMMARY

The present disclosure concerns embodiments of an introducer that is adapted to facilitate insertion of a prosthetic device, such as a prosthetic heart valve, into a patient's vasculature. In particular embodiments, the introducer comprises an elongated body defining a central lumen extending between distal and proximal ends of the body. The body is adapted to be inserted through an incision, such as a transverse aortotomy, and into the vasculature of the patient. A prosthetic valve can be introduced into the patient's vasculature by advancing the valve through the introducer.

The introducer body can have a longitudinally extending gap extending along the length of the body between the distal and proximal ends, which allows the introducer to radially expand and dilate the incision as the valve is advanced through the incision. The gap in the introducer also allows a user to place the introducer around implant sutures by passing the sutures through the gap and into the central lumen. Similarly, the gap allows the introducer to be easily removed from the sutures and/or a delivery device by passing them outwardly through the gap. The introducer body can have a tapered distal portion to facilitate insertion of the introducer through an incision.

In one representative embodiment, a method of implanting a prosthetic heart valve comprises making an incision in the vasculature of a patient's body, threading one or more sutures through a native annulus of the heart and extending the one or more sutures outwardly through the incision and through a portion of the prosthetic valve, placing an introducer around the one or more sutures and inserting the introducer into and through the incision such that a distal end and a proximal end of the introducer are on opposite sides of the incision, sliding the prosthetic valve along the one or more sutures and through the introducer until the prosthetic valve engages the annulus, removing the introducer from the incision, and securing the valve to the annulus with the one or more sutures.

In another representative embodiment, a method of implanting a prosthetic heart valve comprises making an incision in the vasculature of a patient's body, inserting the introducer through the incision and into the vasculature of the patient, and providing a prosthetic valve mounted on a delivery device comprising an elongated handle. The method further comprises advancing the prosthetic valve and a portion of the handle through the introducer until the prosthetic valve engages a native annulus of the heart, and removing the introducer from the incision and away from a position surrounding the handle by passing the handle through a gap formed in a side of the introducer.

In another representative embodiment, an introducer for introducing a prosthetic device into the vasculature of a patient comprises an elongated body having distal and proximal ends and a central passageway extending through the body from the distal end to the proximal end. The body comprises two opposing longitudinal edges defining a gap therebetween, the gap extending from the proximal end to the distal end.

The foregoing and other features and advantages of the invention will become more apparent from the following detailed description, which proceeds with reference to the accompanying figures.

DETAILED DESCRIPTION

The present disclosure concerns embodiments of an introducer that is adapted to facilitate insertion of a prosthetic device, such as a prosthetic heart valve, into a patient's vasculature. The examples described below involve the implantation of a prosthetic valve in the aortic annulus of the heart. However, the introducer can also be used to facilitate implantation of prosthetic valves into the other native annuluses of the heart. Further, the introducer can also be used to introduce various other prosthetic devices into other body lumens.

Figure 2:
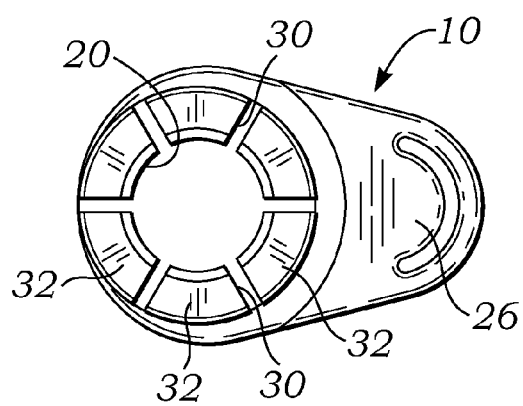
FIG. 2 is a bottom plan view of the introducer shown in FIG. 1.
Figure 1:
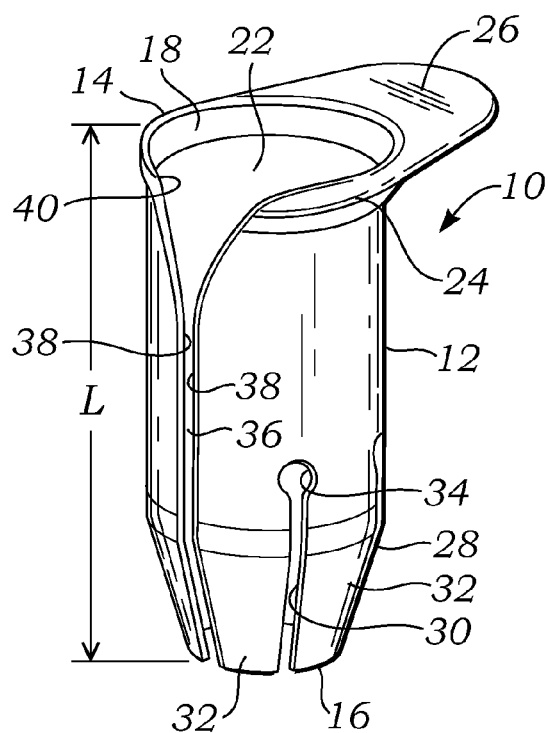
FIG. 1 is a perspective view of an introducer, according to one embodiment, that can be used to introduce a prosthetic heart valve into the vasculature of a patient.

Referring first to FIGS. 1 and 2, an introducer 10, according to one embodiment, comprises an elongated body 12 having a proximal end 14 and a distal end 16. The body 12 has a length L extending from the proximal end 14 to the distal end 16. The body 12 has a proximal opening 18, a distal opening 20, a central lumen, or passageway, 22 extending longitudinally through the body from the proximal opening to the distal opening. The body 12 desirably has a proximal flange 24 that extends circumferentially around the proximal opening and radially outwardly therefrom. The proximal flange 24 can have an enlarged portion 26 that functions as a handle for grasping and manipulating the introducer during use.

The body 12 in the illustrated embodiment has a generally cylindrical shape along the majority of its length and a tapered distal end portion 28 that extends about one third the length of the body. Thus, as can be seen in FIGS. 1 and 2, the proximal opening 18 has a larger diameter than that of the distal opening 20. The tapered distal end portion 28 facilitates insertion of the introducer into a surgical incision, as described below. The body 12 desirably has a plurality of angularly spaced, longitudinally extending gaps 30 defining a plurality of longitudinally extending, circumferentially arrayed fingers 32. The fingers 32 can flex radially outwardly from each other from a non-expanded, or contracted, state (FIG. 1) to an expanded state (FIG. 8) to expand the distal opening to accommodate a prosthetic valve as it is pushed through the distal end portion of the introducer. The proximal end of each gap 30 can terminate at an enlarged circular aperture 34 that facilitates bending or flexing of the fingers at their proximal ends where each finger joins the remaining portion of the body 12.

The body 12 desirably has a longitudinal gap 36 extending the entire length of the body from the proximal end 14 to the distal end 16 and defining longitudinal edges 38. In the illustrated embodiment, the gap 36 has a constant width from the distal end 16 to a location near the proximal end and then flares or widens from this location toward the proximal end 14 to form an enlarged mouth 40 of the gap at the proximal end. The gap 36 allows the introducer 10 to be easily placed around and removed from sutures and/or a delivery device, as further described below. The gap 36 also allows the introducer body 12 to radially expand to accommodate a prosthetic valve having a larger diameter than that of the introducer as the valve is advanced through the introducer. In the illustrated embodiment, the gap 36 can be referred to as a permanent gap because there is a gap or opening between the longitudinal edges 36 when the introducer is in its nonexpanded, or contracted, state shown in FIG. 1.

In an alternative embodiment, the entire length of the gap 36 or a portion thereof can be replaced with a longitudinally extending slit between the longitudinal edges 38. When the body is in a non-expanded state, the edges 38 can contact each other to close the slit. Because the introducer body is made of a flexible material, the edges 38 can be separated to create an opening or gap therebetween, such as for placing the introducer around sutures or a delivery device, as described below. Similarly, the distal end portion 28 can be formed with a plurality of slits defining the fingers 32, rather than permanent gaps 30 between adjacent fingers as shown in the illustrated embodiment.

The introducer 10 can be formed from any of various suitable materials, including metals (e.g., stainless steel or Nitinol), alloys, polymers (e.g., nylon or PTFE), composites, or combinations thereof. In certain embodiments, the introducer can be sized for use with a variety of valve sizes (e.g., 17-35 mm valves). Alternatively, the introducer can be provided in a range of different sizes with each size adapted for use with one valve size or a range of valve sizes.

Figure 3:
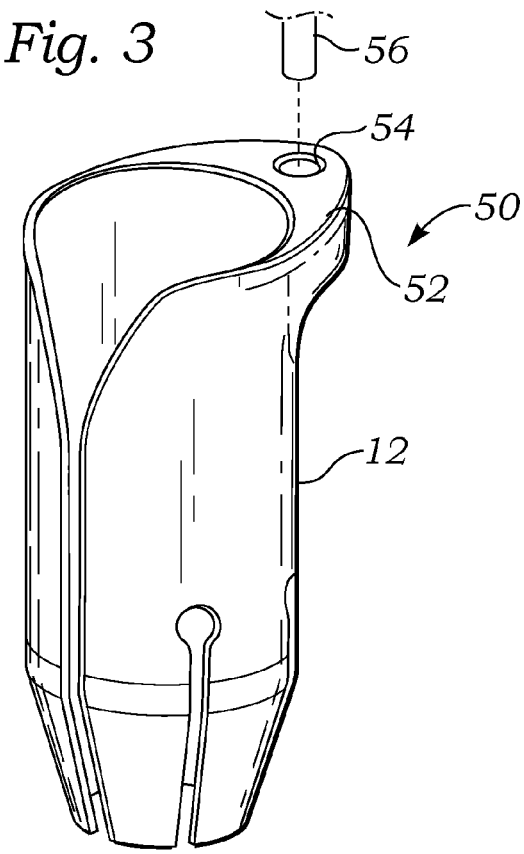
FIG. 3 is a perspective view of another embodiment of an introducer.

FIG. 3 shows an introducer 50, according to another embodiment. The introducer 50 is similar to the introducer 10 shown in FIGS. 1 and 2 in most respects. Unlike the introducer 10, the introducer 50 has a flange portion 52 formed with an opening 54. The opening 54 can be adapted to receive the distal end of an elongated handle 56 that can be used to assist in positioning and manipulating the introducer during use.

FIGS. 4-11 illustrate the use of the introducer 10 in one specific procedure for implanting a prosthetic heart valve 60 in the aortic annulus. The prosthetic valve 60 in the illustrated embodiment includes a substantially rigid, non-collapsible annular frame 62, a plurality of leaflets 64 supported by the frame, a sewing ring 66, and a plastically expandable stent, or support frame, 68 extending downwardly from the sewing ring. The prosthetic valve 60 can be referred to as a hybrid valve in that it combines a non-collapsible surgical valve and an expandable stent that is typically incorporated in expandable prosthetic valves that are delivered in minimally invasive procedures. The prosthetic valve 60 can be mounted to the distal end of an elongated shaft or handle of a delivery device 72. Exemplary embodiments of the prosthetic valve 60 and the delivery device 72 are further described in U.S. Patent Publication No. 2010/0249894, filed Mar. 3, 2010, and U.S. Pat. No. 8,348,998, filed Jun. 23, 2010, which are incorporated herein by reference.

Figure 4:
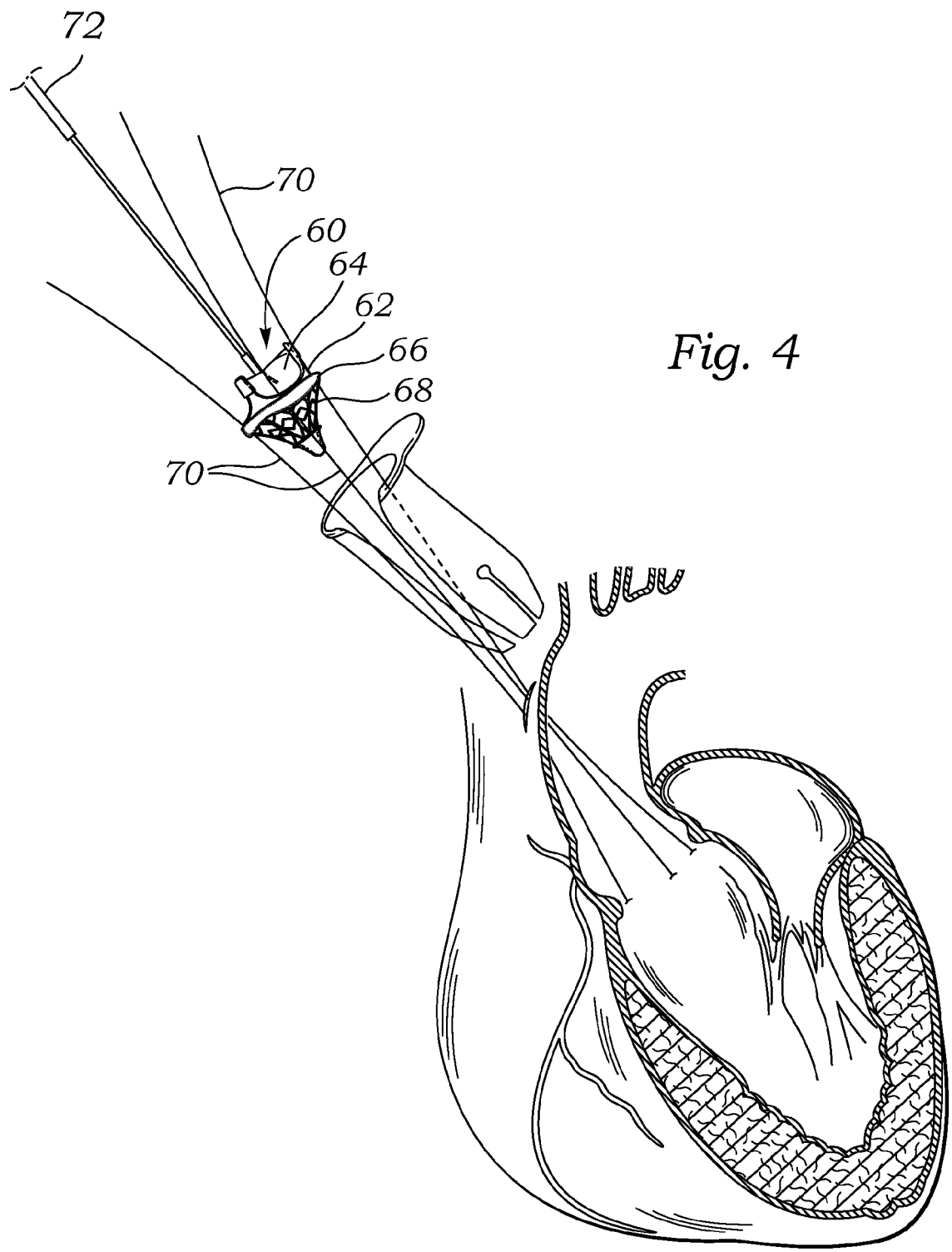
FIGS. 4-10 illustrate one specific procedure for implanting a prosthetic aortic valve into the heart using the introducer shown in FIG. 1.

As shown in FIG. 4, an incision can be made in the aorta to access the aortic annulus. Typically, although not required, the native leaflets are excised before implanting the prosthetic valve, as shown in the figures. A plurality of implant sutures 70 can be threaded through the periphery of the aortic annulus, extended outside of the body through the incision and then threaded through the sewing ring 66 of the prosthetic valve 60 in a conventional manner. It has been found that three implant sutures are sufficient to adequately secure the prosthetic valve in place at the implantation site when the securement of the valve to the annulus is supplemented by the stent 68. A greater or fewer number of implant sutures can be used in other applications.

Figure 5:
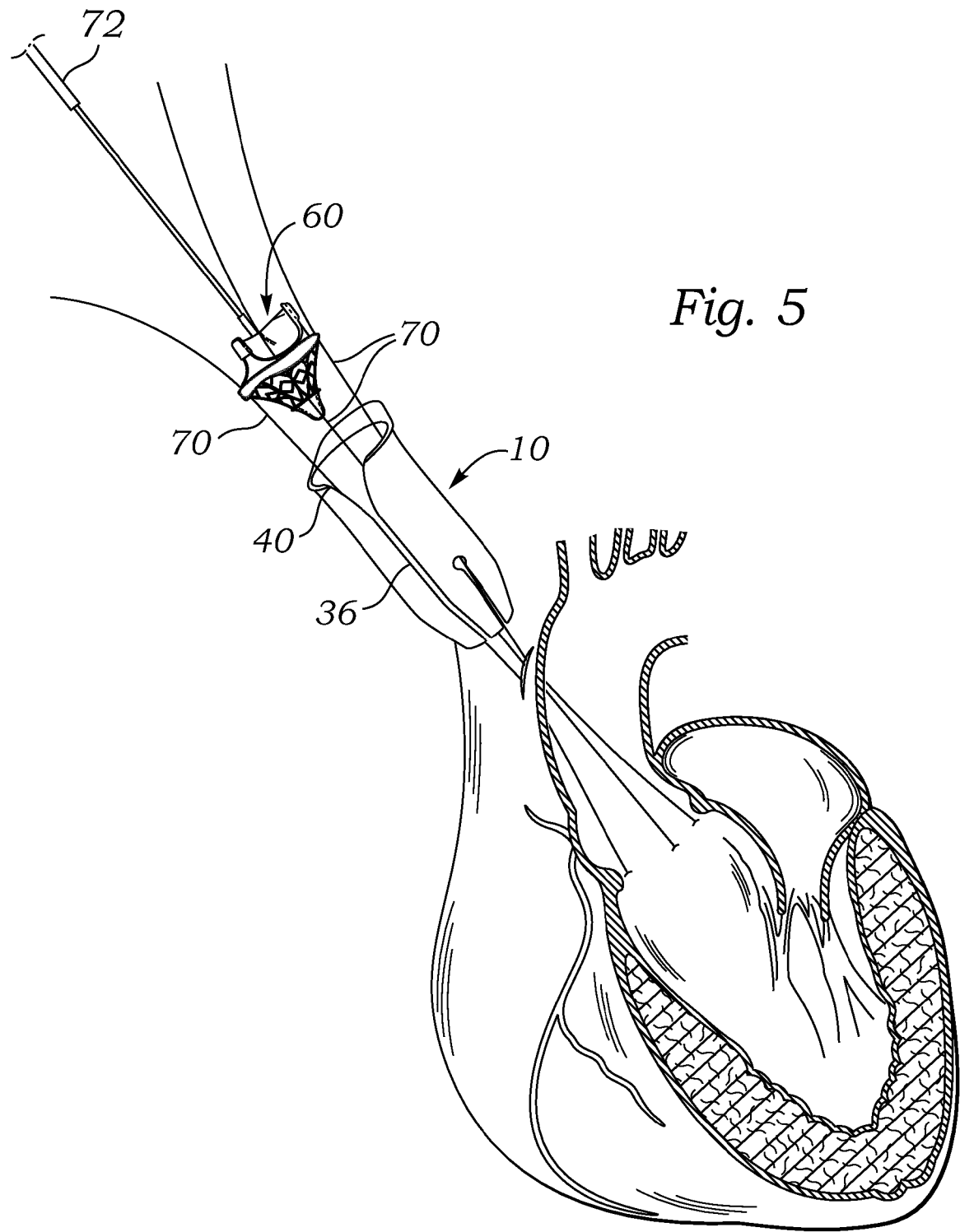

To assist in passing the prosthetic valve 60 through the incision in the aorta using the introducer, the introducer 10 is first placed around the sutures 70 and inserted through the incision. Because the introducer has a gap 36 extending the length of the introducer, it can be easily placed around the sutures at a location between the incision and the valve by passing the sutures through the gap 36, as depicted in FIGS. 4 and 5. The enlarged mouth portion 40 of the gap facilitates this process in that it allows the operator to more easily direct the implant sutures 70 into and through the gap 36.

Figure 6:
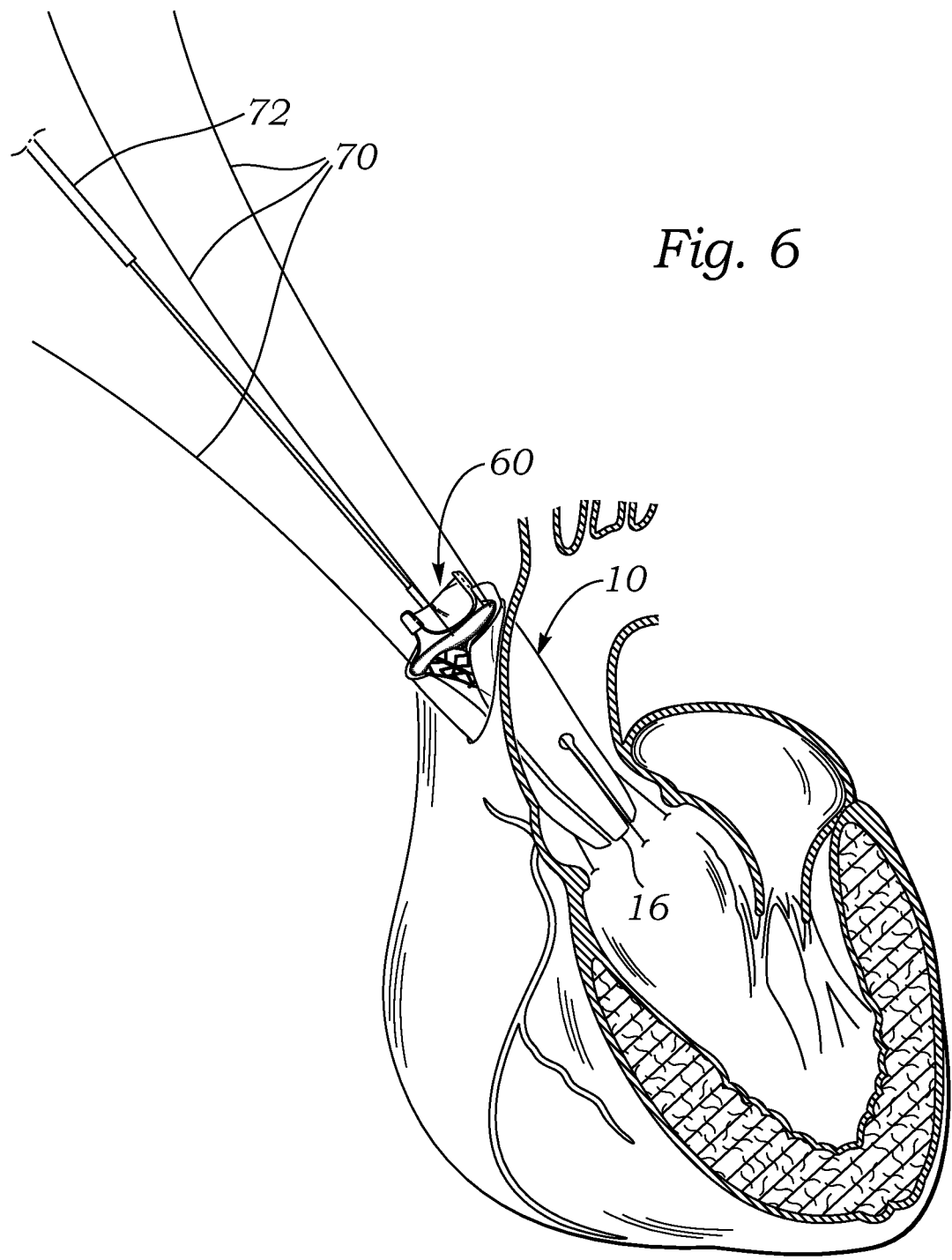
Figure 7:
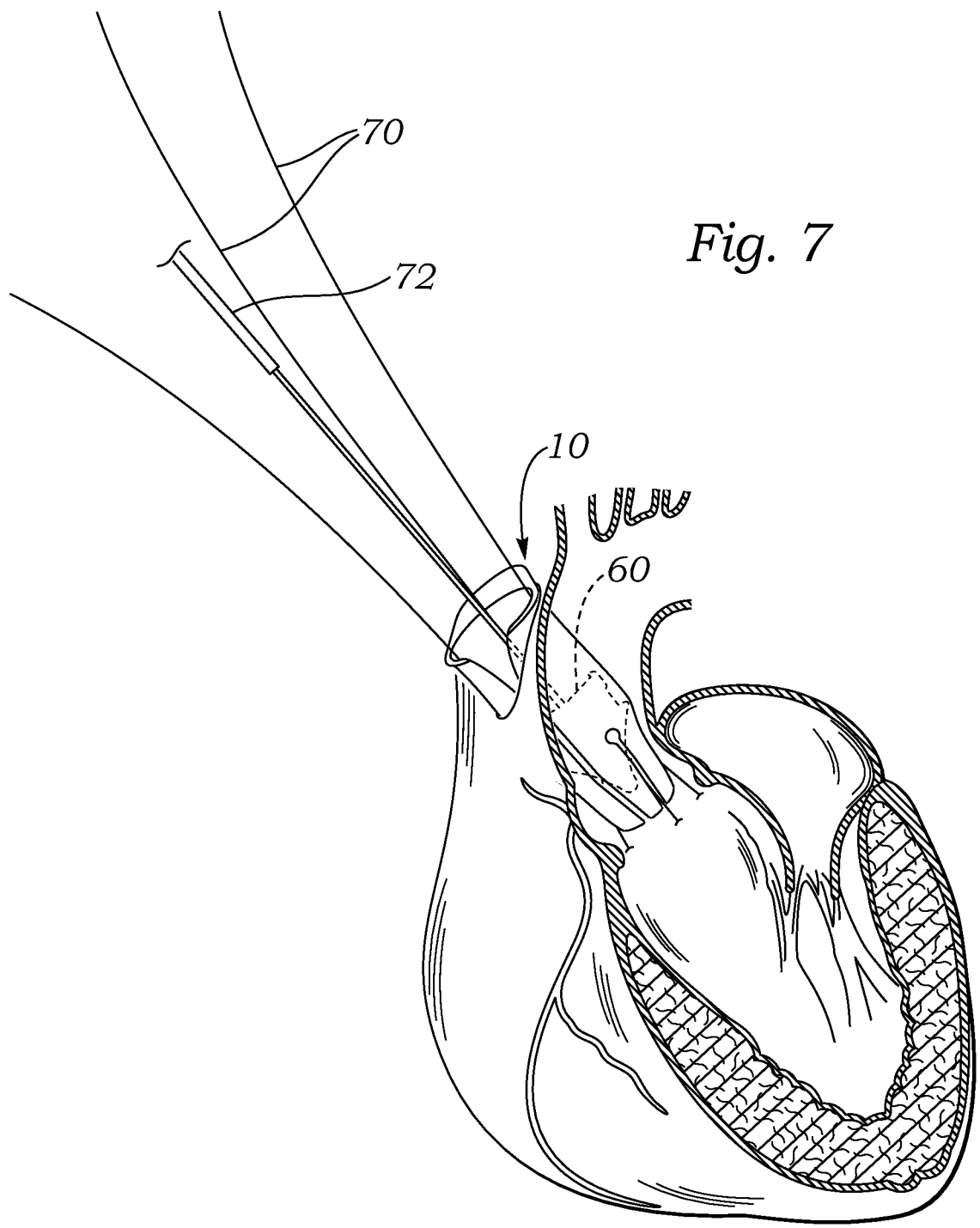
Figure 8:
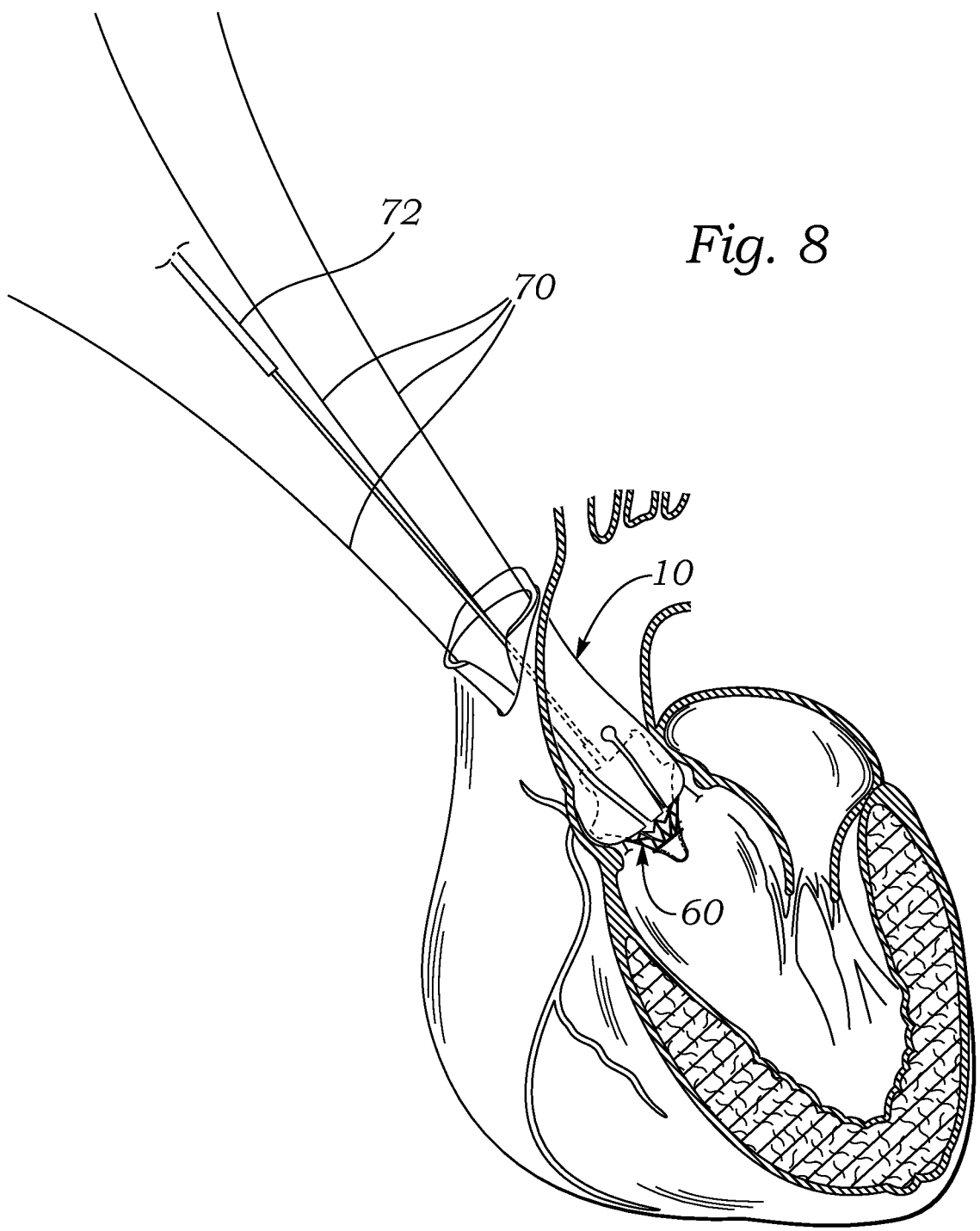

As shown in FIG. 6, the introducer 10 can then be inserted through the incision into the aorta. The tapered distal end portion 28 facilitates the insertion of the introducer through the incision. The introducer desirably is positioned such that the distal end 16 is positioned in the native annulus or in the Valsalva sinuses immediately adjacent the native annulus. In this manner, the prosthetic valve can be guided directly to the desired implantation position as it is advanced from the distal end of the introducer. After the introducer is inserted into the aorta, the surgeon can push the prosthetic valve through the introducer and into the aorta. If the outer diameter of the prosthetic valve 60 is greater than the diameter of the introducer, the introducer can radially expand as the prosthetic valve passes through the introducer due to the presence of the gap 36, as depicted in FIGS. 6-8. In addition the fingers 32 can expand radially outwardly from each other to accommodate the passage of the valve through the tapered distal end portion 28 of the introducer.

In the illustrated example, the incision can be made smaller than the cross-sectional profile of the prosthetic valve taken at sewing ring 66 (the cross-sectional profile is taken at a plane that extends through the sewing ring and is perpendicular to the central axis of the valve). Thus, as the valve passes through the incision in this example, the incision is caused to dilate by the radial force of the valve against the introducer, allowing the valve to slide through the introducer at the location of the incision while minimizing or preventing laceration of the tissue. Moreover, the prosthetic valve can be pushed through the incision while the valve is maintained at a position in which the cross-sectional profile of the valve is generally perpendicular to the line of movement through the introducer and the incision; in other words, the valve need not be tilted or canted in order to pass the valve through the incision, as required to perform a conventional "shoehorn" technique.

Figure 9:
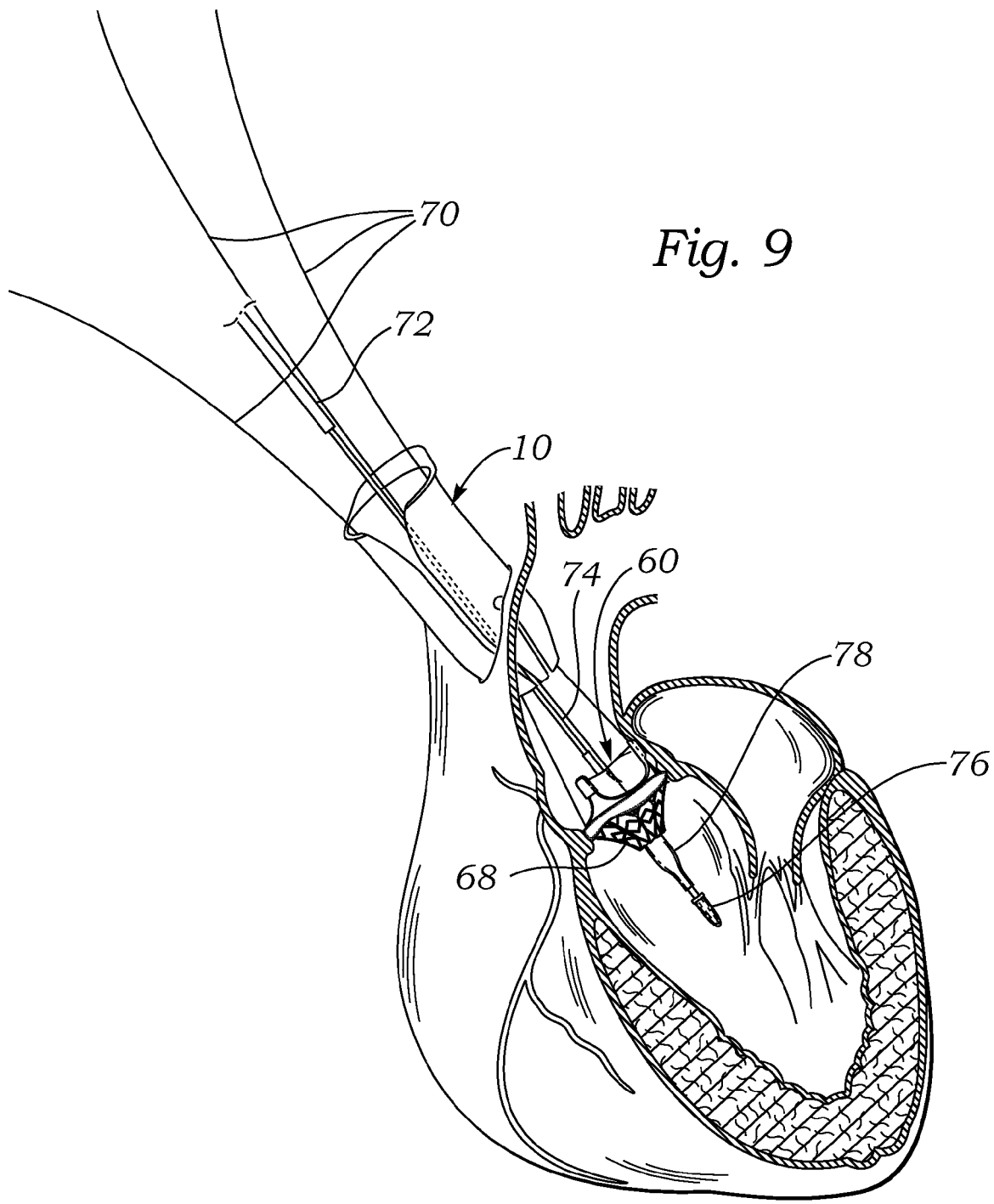
Figure 10:
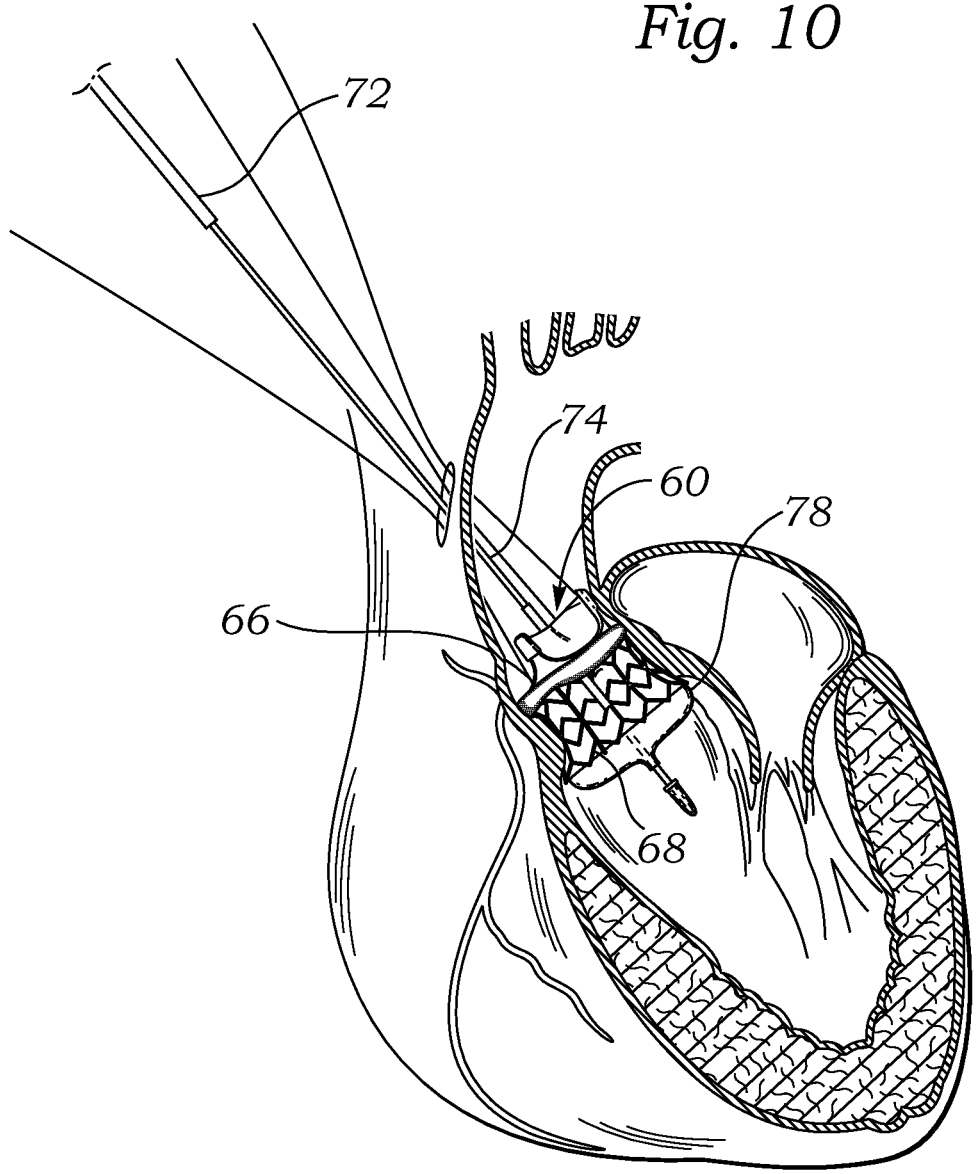

As shown in FIG. 9, the valve can be advanced out of the distal end of the introducer 10 and seated against the aortic annulus. At this time, the introducer 10 can be removed from the incision and from its position extending around the sutures 70 and the delivery device 72. The introducer can be removed from its position extending around the sutures 70 and the delivery device 72 by simply withdrawing the introducer laterally away from the sutures and the delivery device while directing them to pass through the gap 36 in the introducer. Due to the presence of the gap, the introducer can be removed sideways with respect to the delivery device and does not need to be withdrawn off of the proximal end of the delivery device, which is being held in one hand of the surgeon. Advantageously, this allows the surgeon to easily and quickly remove the introducer without having to remove the hand from the proximal end of the delivery device.

As further shown in FIG. 9, after removing the introducer 10, the expandable stent 68 can be deployed by advancing a balloon catheter 74 of the delivery device proximally relative to the valve to displace a nose cone 76 out of engagement with the stent 68 and to position a balloon 78 of the balloon catheter to extend through the stent 68. The balloon 78 can then be inflated to cause the stent 68 to radially expand and engage surrounding tissue. Thereafter, the balloon is deflated, the sutures 70 are tied off to secure the sewing ring 66 to the aortic annulus, and the delivery device is detached from the valve 60 and removed from the body. As can be appreciated, in the illustrated example, the prosthetic valve is secured in place against the native annulus by a combination of the sutures 70 and the radial outward force of the expandable stent 68.

It can be appreciated that the introducer can be used to assist in the implantation of other types of prosthetic valves. For example, the introducer can be used to introduce a conventional surgical valve (i.e., one that does not have an expandable stent, like stent 68 of valve 60) into the patient's vasculature. When implanting a conventional surgical valve, a greater number of implant sutures 70, typically about 15-21 sutures, are used to secure the valve to the native annulus. The introducer can also be used to introduce into a patient's vasculature a transcatheter heart valve that can be radially compressed to a reduced diameter for insertion into the patient's vasculature and radially expandable to its functional size at the deployment site inside the body.

Figure 11:
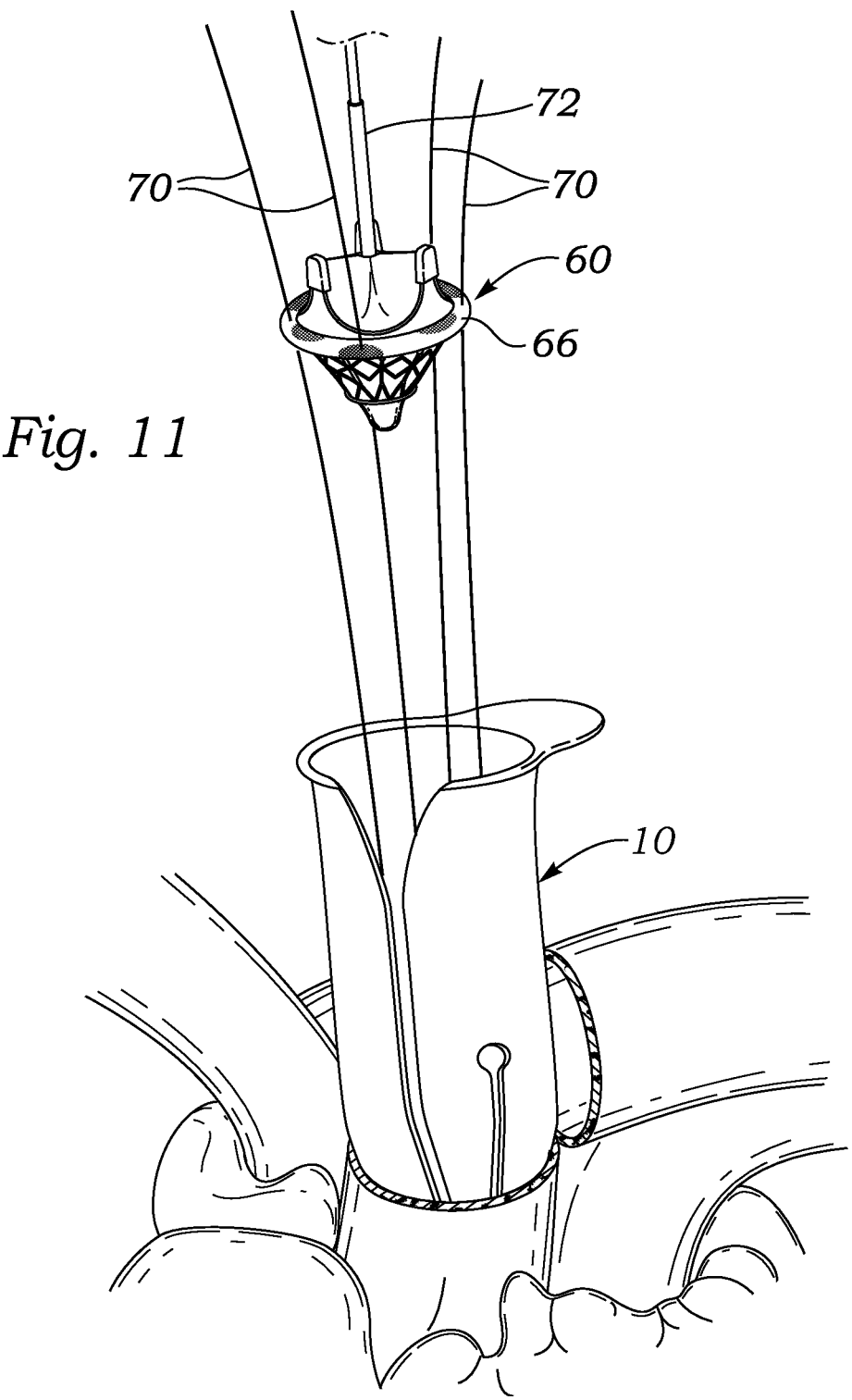
FIG. 11 illustrates another procedure for implanting a prosthetic aortic valve into the heart using the introducer shown in FIG. 1.

In addition, the introducer 10 can be used introduce a valve into the patient's vasculature via any type of aortotomy (incision in the aorta). For example, FIG. 11 illustrates the implantation of a prosthetic valve 60 via a transverse aortotomy where a transverse incision is made through the aortic root. A plurality of implant sutures can be threaded through the native annulus and the sewing ring 66 of the valve, as described above. As shown, the introducer 10 can be placed around the sutures by passing the sutures through the gap 36, and then inserting the distal end portion 28 of the introducer into the aortic root until the distal end is just above the native annulus. The prosthetic valve 60 can then be pushed through the introducer, into the aorta and into the native annulus. The valve can be secured in place by deploying the stent 68 and tying off the implant sutures 70, as described above. If the prosthetic valve has a diameter greater than that of the portion of the aorta through which the valve passes, the introducer 10 causes the aorta to dilate around the valve as it is passed through the introducer toward the annulus, thereby allowing for atraumatic passage of the valve and protecting against damage to the valve itself. Moreover, the valve can be introduced while held perpendicular to the line of movement into and through the aorta; that is, the valve need not be tilted or canted relative to the line of movement in order pass the relatively larger valve into the aorta.

Figure 12:
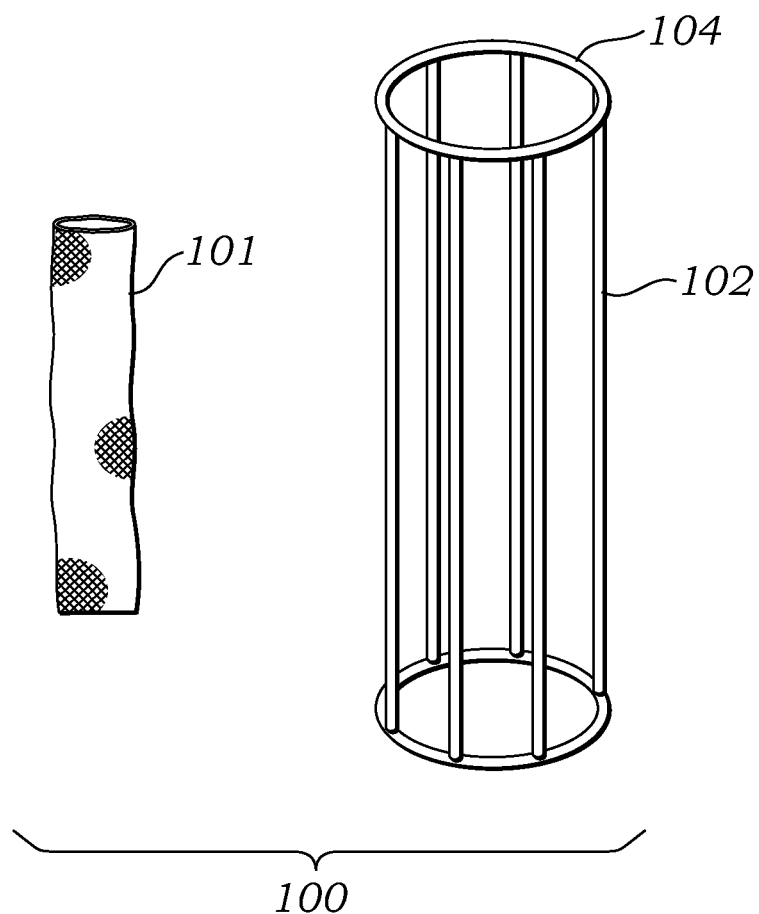
FIG. 12 shows an introducer assembly, according to another embodiment, that can be used to introduce a prosthetic heart valve into the vasculature of a patient.

FIG. 12 illustrates an introducer assembly 100, according to another embodiment, that can be used to introduce a prosthetic device, such as a prosthetic valve 60, into the vasculature of a patient. The assembly 100 in the illustrated embodiment comprises an introducer 101 (also referred to as a sleeve) and an applicator frame, or mounting frame, 102 configured to mount the introducer 101 around the prosthetic valve. The introducer 101 can comprise a tubular sleeve made of a stretchable, flexible and/or resilient material, such as a fabric. The applicator 102 is configured to retain the introducer 101 in an expanded state having a generally cylindrical configuration to allow the prosthetic valve to be placed within the introducer during use. The applicator 102 can comprise proximal and distal rings 104, 106, respectively, interconnected by a plurality of longitudinal members 108 extending between and interconnecting the rings. The applicator 102 desirably is made of a relatively rigid material as compared to the introducer, such as metal or plastic.

Figure 13:
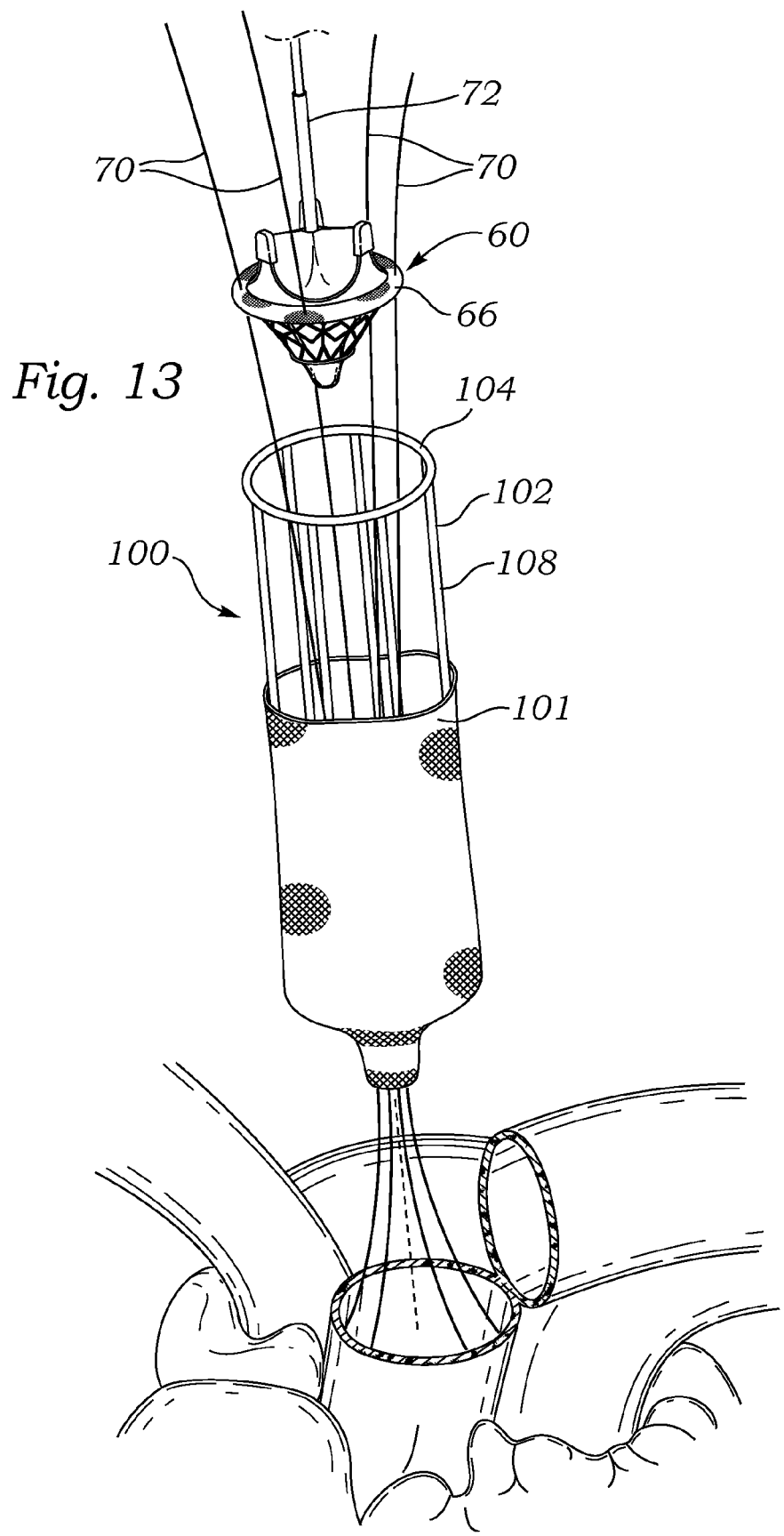
FIGS. 13-17 illustrate one specific procedure for implanting a prosthetic aortic valve into the heart using the introducer assembly shown in FIG. 12.

FIGS. 13-17 illustrate the implantation of the valve into the aortic annulus via a transverse aortotomy made at the aortic root. However, it should be understood that various other aortotmies can be performed to gain access to the native annulus for implanting the prosthetic valve using the introducer assembly 100. In any case, as shown in FIG. 13, implant sutures 70 can be threaded through the native annulus and the sewing ring 66 of the valve. The introducer 101 is first placed around the applicator 102, and the assembly 100 is placed around the sutures 70, as depicted in FIG. 13, by inserting the proximal ends of the sutures 70 and the delivery device (the proximal ends are not shown in FIG. 13) into the distal opening of the applicator 102 and sliding the assembly downwardly to the position shown in FIG. 13. The inner diameter of the applicator 102 (defined by proximal and distal rings 104, 106) is dimensioned large enough to permit the valve to pass easily through the applicator.

Figure 14:
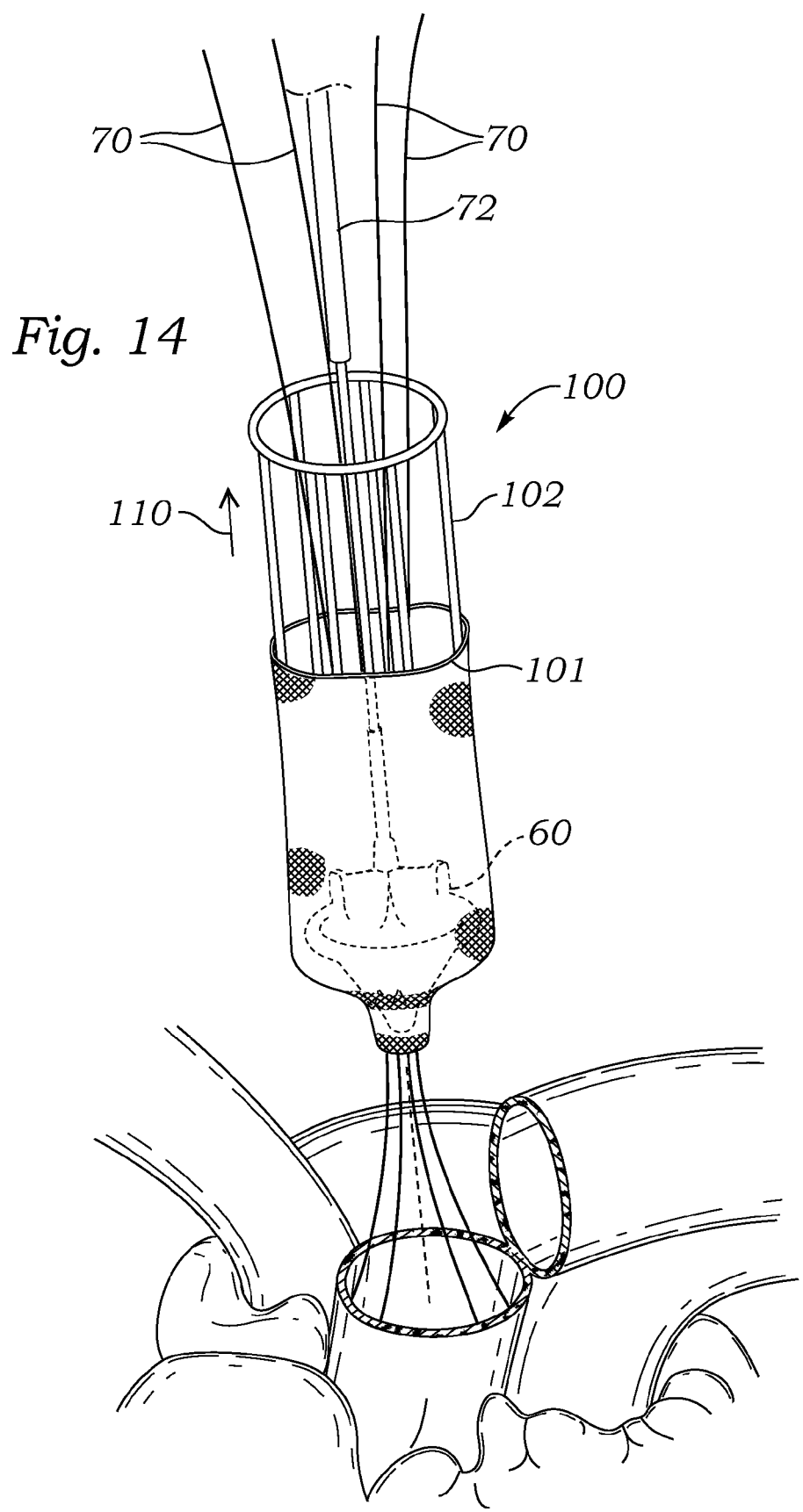
Figure 15:
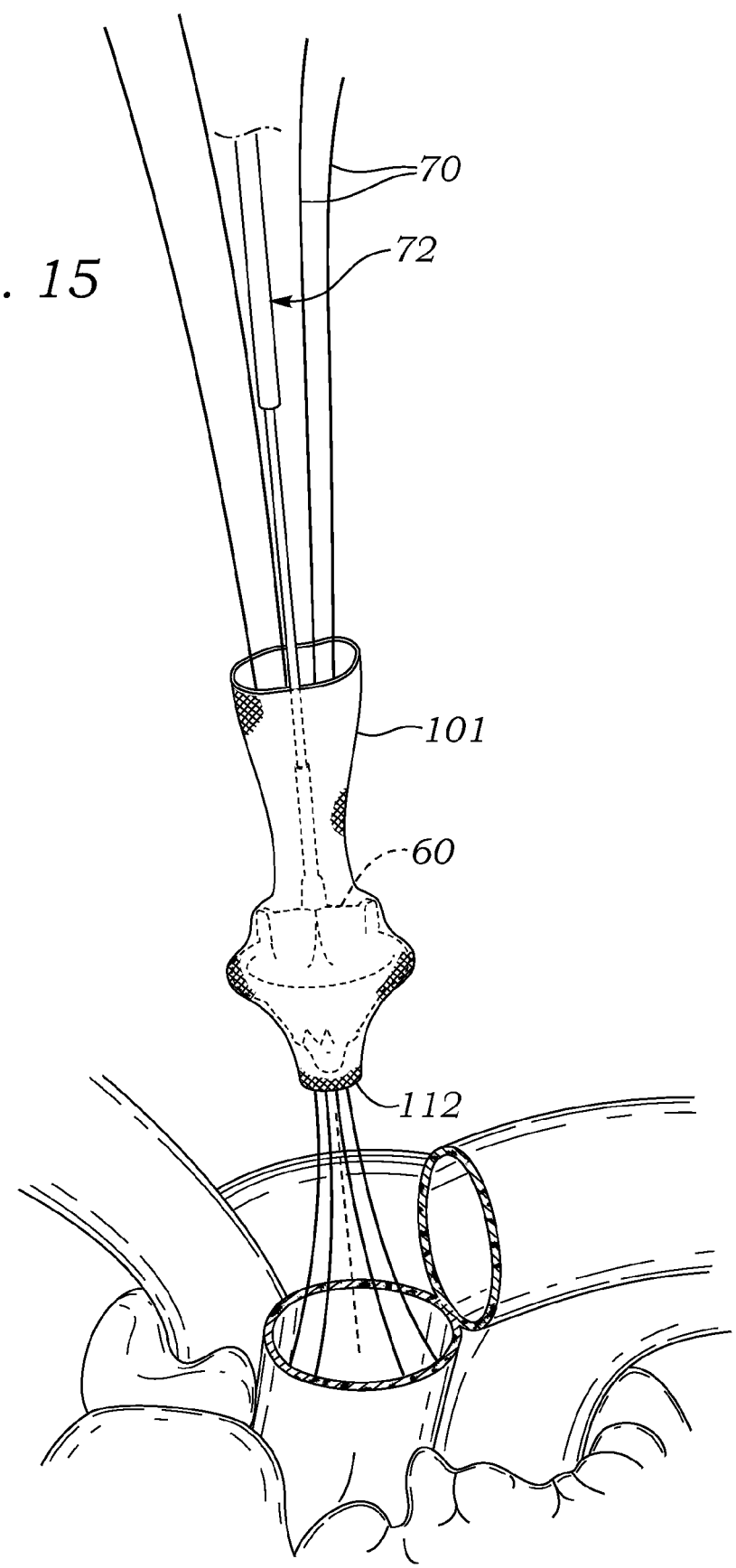

Referring to FIG. 14, the valve 60 can then be positioned within the expanded introducer 101. With the valve inside of the introducer 101, the introducer is removed from the applicator, such as by holding the introducer and the valve stationary and retracting the applicator 102 upwardly in the direction of arrow 110. The applicator 102 can be removed from its position surrounding the sutures and the delivery device 72 by withdrawing the applicator upwardly beyond the proximal ends of the sutures and the delivery device. When the applicator is removed, the introducer 101 collapses around and desirably extends over and covers the entire valve such that a distal end portion 112 of the introducer extends beyond the lower end of the valve, as depicted in FIG. 15.

Figure 16:
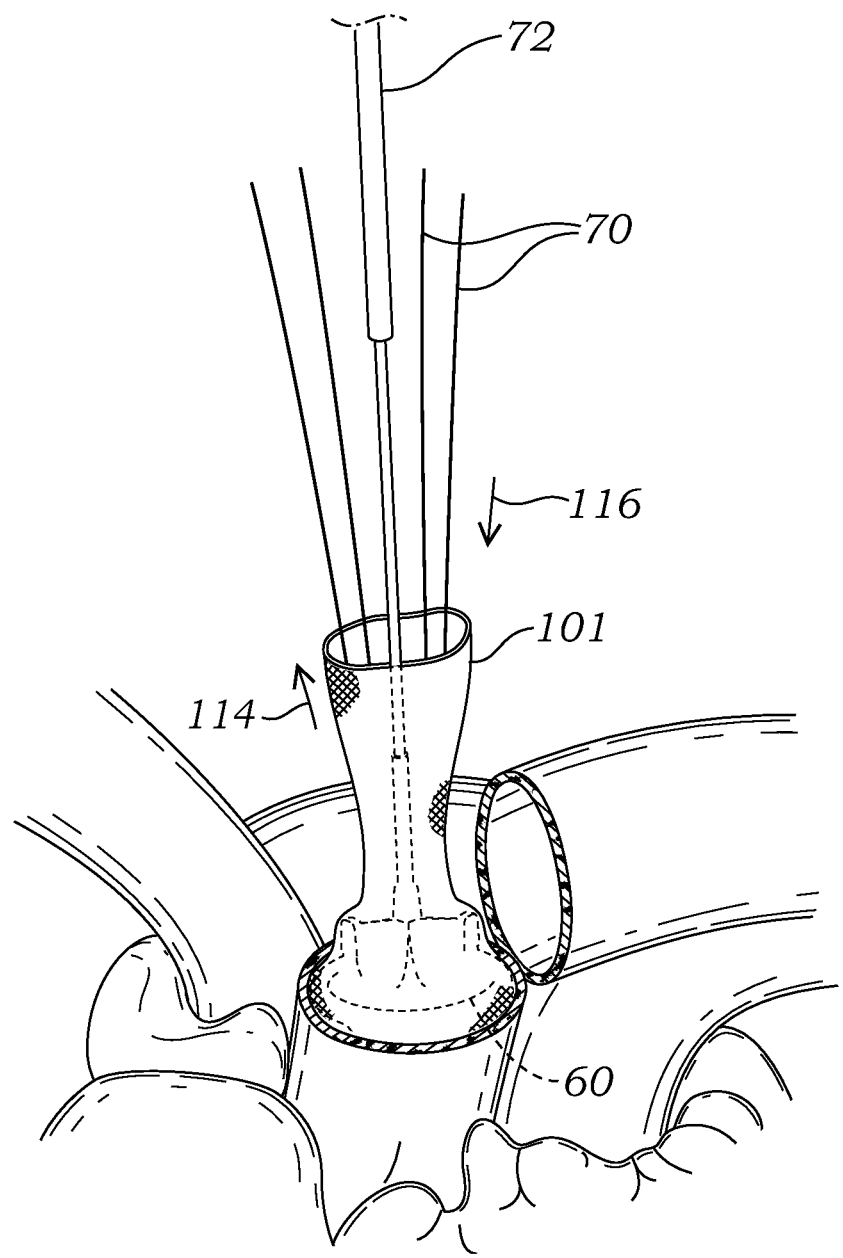
Figure 17:
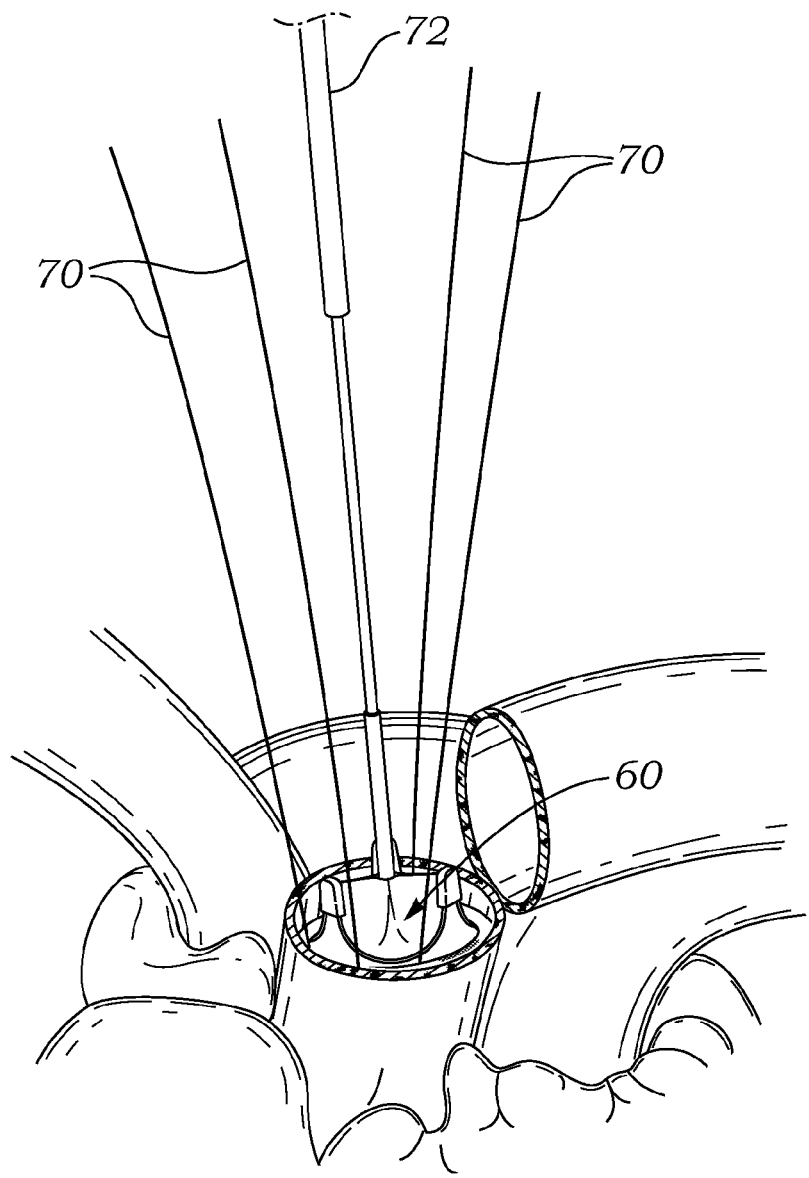

Referring to FIG. 16, the distal end portion of the introducer 101 is then inserted into the aortic root. The valve 60 can then be inserted into the aortic root by maintaining slight upward tension on the introducer 101 (in the direction of arrow 114) while pushing downwardly on the valve 60 via the delivery device (in the direction of arrow 116). As the valve is pushed through the introducer and into the aortic root, the vessel dilates and allows the valve to be advanced through the vessel to the implantation site at the aortic annulus. When the valve is at the desired position, the valve is held firmly in place via the delivery device and the introducer 101 is pulled out of the aortic root and then removed from the delivery device (FIG. 17) by moving the introducer upwardly beyond the proximal ends of the suture and the delivery device and the sutures. Thereafter, the valve can be secured in place by deploying the stent 68 and tying off the implant sutures 70, as described above.

Figure 18:
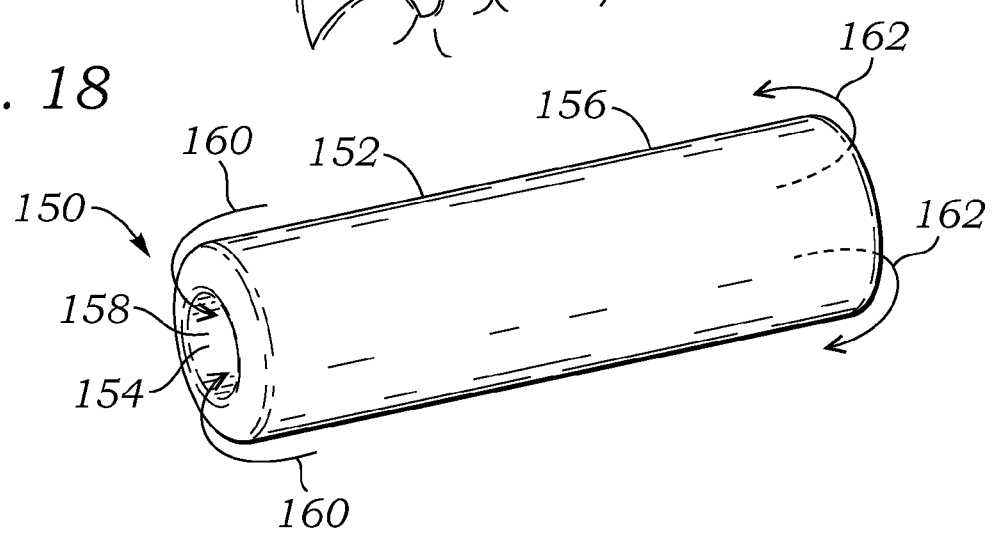
FIG. 18 is a perspective view of another embodiment of an introducer that can be used to introduce a prosthetic heart valve into the vasculature of a patient.

FIG. 18 shows an introducer 150, according to another embodiment, that can be used to introduce a prosthetic device, such as a prosthetic valve 60, into the vasculature of a patient. The introducer 150 comprises a thin-walled, generally tubular body 152 defining a central lumen, or passageway, 154. The introducer body 152 is constructed from a thin membrane made of a flexible material, such as a flexible polymer, that forms a tubular outer membrane 156 and a tubular inner membrane 158. The outer and inner membranes are joined to each other at the opposite ends of the body so as to form a sealed inner cavity that can contain a fluid, such as a sterile liquid. The introducer body exhibits sufficient flexibility to allow the positions of the inner and outer members to be reversed; that is, the outer membrane 156 can be turned and pushed inwardly into the lumen 154 at one end of the body to become part of the inner membrane (as indicated by arrows 160) while the inner membrane 158 at the opposite end of the body is caused to turn and move outwardly (as indicated by arrows 162) so as to become part of the outer membrane.

In use, a prosthetic valve 60 (or other prosthetic device), which can be mounted to the distal end of a delivery device as described herein, can be inserted into the lumen 154 of the introducer 150. This can be accomplished by pushing or urging the valve into the opening at one end of the introducer. The rolling or reversing action of the membranes causes the introducer to "roll" onto and over the valve. With the introducer 150 covering the valve, one end of the introducer is inserted into an incision made in the aorta (or another part of the patient's vasculature). The valve can then be pushed through the introducer and into the aorta. As the valve is advanced through the introducer, the membranes 156, 158 can roll relative to the valve to facilitate its passage through the lumen 154.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of implanting a prosthetic heart valve comprising:
    making an incision in the vasculature of a patient's body;
    threading one or more sutures through a native annulus of the heart and extending the one or more sutures outwardly through the incision and through a portion of a prosthetic valve having a non-collapsible/non-expandable annular frame;
    providing an introducer comprising an elongated body, a central passageway extending through the body, the elongated body having on one side two opposing longitudinal edges that are not connected from the proximal end to the distal end and face each other to form a longitudinally extending gap or slit therebetween;
    placing an introducer around the one or more sutures by passing the one or more sutures between the two opposing longitudinal edges in the introducer body and into the central passageway of the introducer;
    inserting the introducer into and through the incision such that a distal end and a proximal end of the introducer are on opposite sides of the incision;
    sliding the prosthetic valve along the one or more sutures and through the introducer until the prosthetic valve engages the annulus;
    removing the introducer from the incision; and
    securing the valve to the annulus with the one or more sutures.

2. The method of claim 1, further comprising, after removing the introducer from the incision, removing the introducer from a position surrounding the one or more sutures by passing the one or more sutures outwardly between the two opposing longitudinal edges in the introducer body.

3. The method of claim 1, wherein the distance between the two opposing longitudinal edges widens from a first width at a location spaced from the proximal end to a second, greater width at the proximal end.

4. The method of claim 1, wherein the act of inserting the introducer into and through the incision comprises positioning the distal end of the introducer in or immediately adjacent the native annulus.

5. The method of claim 1, wherein the introducer body is expandable and sliding the prosthetic valve through the introducer causes the introducer body to radially expand.

6. The method of claim 1, further comprising radially expanding a stent of the prosthetic valve against the annulus to further anchor the valve to the annulus.

7. A method of implanting a prosthetic heart valve comprising:
- making an incision in the vasculature of a patient's body;
- threading an array of sutures through a native annulus of the heart and extending the sutures outwardly through the incision and through a portion of a prosthetic valve having a non-collapsible/non-expandable annular frame and a diameter that is larger than a relaxed diameter of the introducer;
- providing an expandable introducer having a generally tubular body defining a longitudinal passageway from the proximal end to the distal end and two parallel and opposing longitudinal edges in the introducer body;
- laterally passing the introducer around the array of sutures between the native annulus and the prosthetic valve between the longitudinal edges in the introducer body and into the longitudinal passageway of the introducer;
- inserting the distal end of the introducer into and through the incision such that the distal end and the proximal end are on opposite sides of the incision
- connecting an elongated handle to the prosthetic valve;
- parachuting the prosthetic valve down the array of sutures and through the longitudinal passageway of the introducer until it rests against the native annulus, the prosthetic valve expanding the introducer by spreading apart the longitudinal edges as it passes therethrough; and
- securing the prosthetic valve to the annulus.

8. The method of claim 7, wherein prior to the act of advancing the prosthetic valve and a portion of the handle through the introducer, the method further comprises threading one or more sutures through the native annulus and a sewing ring of the prosthetic valve and placing the introducer around the one or more sutures by passing the one or more sutures between two opposing longitudinal edges in the introducer body and into a central lumen of the introducer.

9. The method of claim 8, further comprising removing the introducer from the incision and removing the introducer from a position surrounding the sutures and handle by passing the sutures and handle outwardly between the two opposing longitudinal edges in the introducer body.

10. The method of claim 7, wherein the introducer comprises a tapered distal end portion, the distal end portion comprising a plurality of circumferentially arrayed, radially expandable fingers having distal ends defining a distal opening of the introducer, the fingers radially expanding from a non-expanded state to an expanded state as the prosthetic valve is advanced through the distal end portion.

11. The method of claim 7, wherein advancing the prosthetic valve through the introducer causes the introducer body to radially expand by displacement of two opposing longitudinal edges in the body that are not connected from the proximal end to the distal end.

12. The method of claim 11, wherein the distance between the two opposing longitudinal edges widens from a first width at a location spaced from the proximal end to a second, greater width at the proximal end.

13. The method of claim 7, wherein the step of securing the prosthetic valve to the annulus includes balloon-expanding a stent extending from an inflow end of the prosthetic valve.

14. The method of claim 13, wherein the native annulus of the heart is the aortic annulus and the incision is made in the ascending aorta.

* * * * *